(12) United States Patent
Julius

(10) Patent No.: US 8,123,712 B2
(45) Date of Patent: Feb. 28, 2012

(54) CONTROLLABLE SWAB DEVICE

(75) Inventor: Robert P. Julius, Greenwich, CT (US)

(73) Assignee: Professional Disposables International, Inc., Orangeburg, NY (US)

( * ) Notice: Subject to any disclaimer, the term of this patent is extended or adjusted under 35 U.S.C. 154(b) by 914 days.

(21) Appl. No.: 11/713,536

(22) Filed: Mar. 2, 2007

(65) Prior Publication Data

US 2008/0214977 A1 Sep. 4, 2008

(51) Int. Cl.
*A61M 35/00* (2006.01)

(52) U.S. Cl. .............................................. 604/1; 15/172

(58) Field of Classification Search .................. 604/1–3; 127/65; 15/167.1, 172, 210.1

See application file for complete search history.

(56) References Cited

U.S. PATENT DOCUMENTS 1,369,664 A * 2/1921 Izawa ........................... 15/167.1

(Continued)

FOREIGN PATENT DOCUMENTS

WO 9421152 A1 9/1994

OTHER PUBLICATIONS

Wynne, Diana. 'Re: the folding spoon'. The Daily Interface [online]. Availabe on the Web as of Sep. 2006 [retrieved on Jun. 23, 2009]. Retrieved from the Internet:http://dailyinterface.blogspot.com/2006/09/folding-spoon.html.*

*Primary Examiner* — Tatyana Zalukaeva
*Assistant Examiner* — Benedict L Hanrahan
(74) *Attorney, Agent, or Firm* — St. Onge Steward Johnston & Reens LLC

(57) ABSTRACT

An improved swab device includes a handle member having a swab portion and a hinge. The hinge divides the handle member into a handle portion and a controllable portion. The device further includes a first stop member and a second stop member. The controllable portion may articulate from a rest position in a first direction until it is retained in a first retained position. The first stop member is configured to prohibit the swab portion from articulating any further in a first direction and also may be configured to maintain the swab portion in the first retained position. The swab portion may then be released from the first retained position and articulate in an opposite second direction until it is retained in a second position. The second stop member is configured to prohibit the swab from articulating any further in a second direction and also may be configured to maintain the swab portion in the second retained position.

11 Claims, 3 Drawing Sheets

U.S. PATENT DOCUMENTS

| | | |
|---|---|---|
| 4,165,755 A | 8/1979 | Cassai |
| 4,283,809 A | 8/1981 | Prost |
| 4,712,266 A * | 12/1987 | Yamaki ........................ 15/167.1 |
| 4,731,896 A * | 3/1988 | de La Tour ...................... 15/106 |
| 5,158,532 A | 10/1992 | Peng et al. |
| 5,615,440 A | 4/1997 | Cowan et al. |
| 5,671,497 A | 9/1997 | Abdo |
| 5,762,494 A | 6/1998 | Archambault |
| 5,797,899 A * | 8/1998 | Tilton, Jr. .......................... 606/1 |
| 6,416,506 B1 | 7/2002 | Tilton, Jr. et al. |
| 6,758,618 B2 | 7/2004 | Petrich et al. |
| 6,941,607 B1 | 9/2005 | Berglass |
| 7,211,061 B1 * | 5/2007 | Maxwell ........................... 604/1 |
| 2003/0108846 A1 * | 6/2003 | Hoertsch ....................... 433/216 |

* cited by examiner

FIG. 1
FIG. 1A
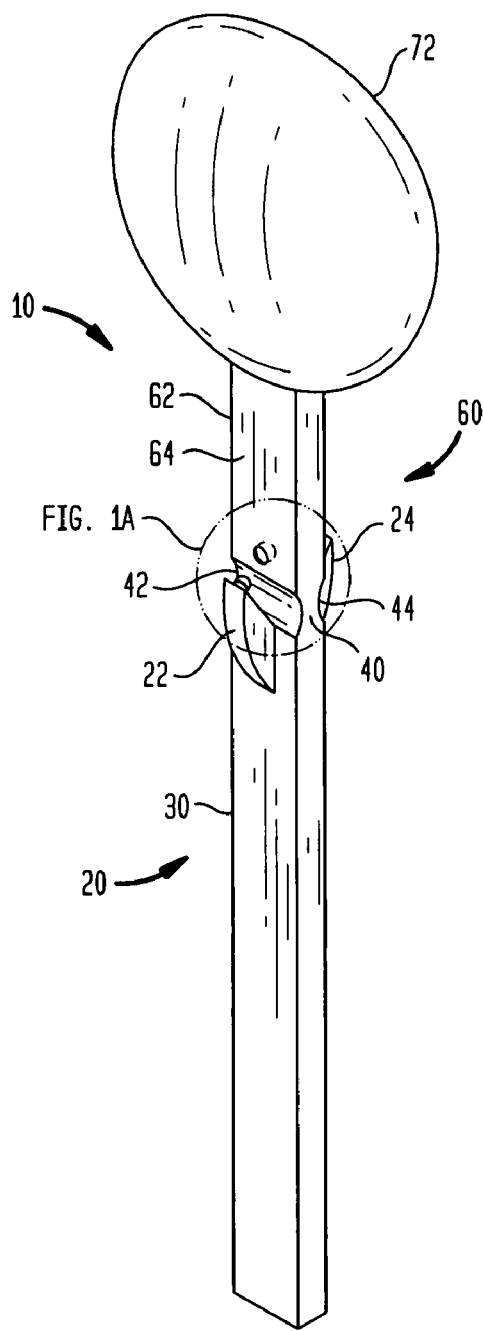
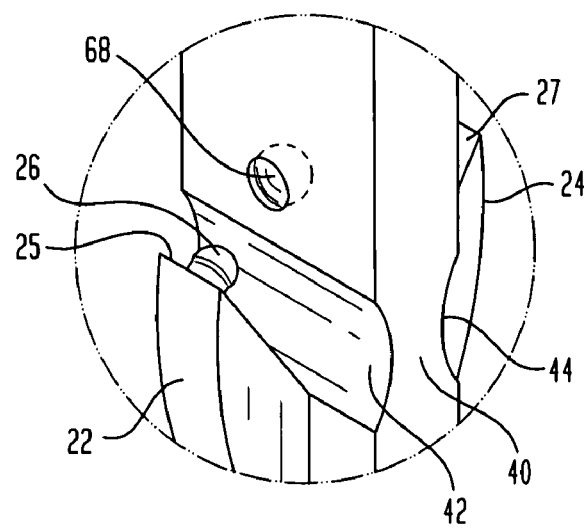

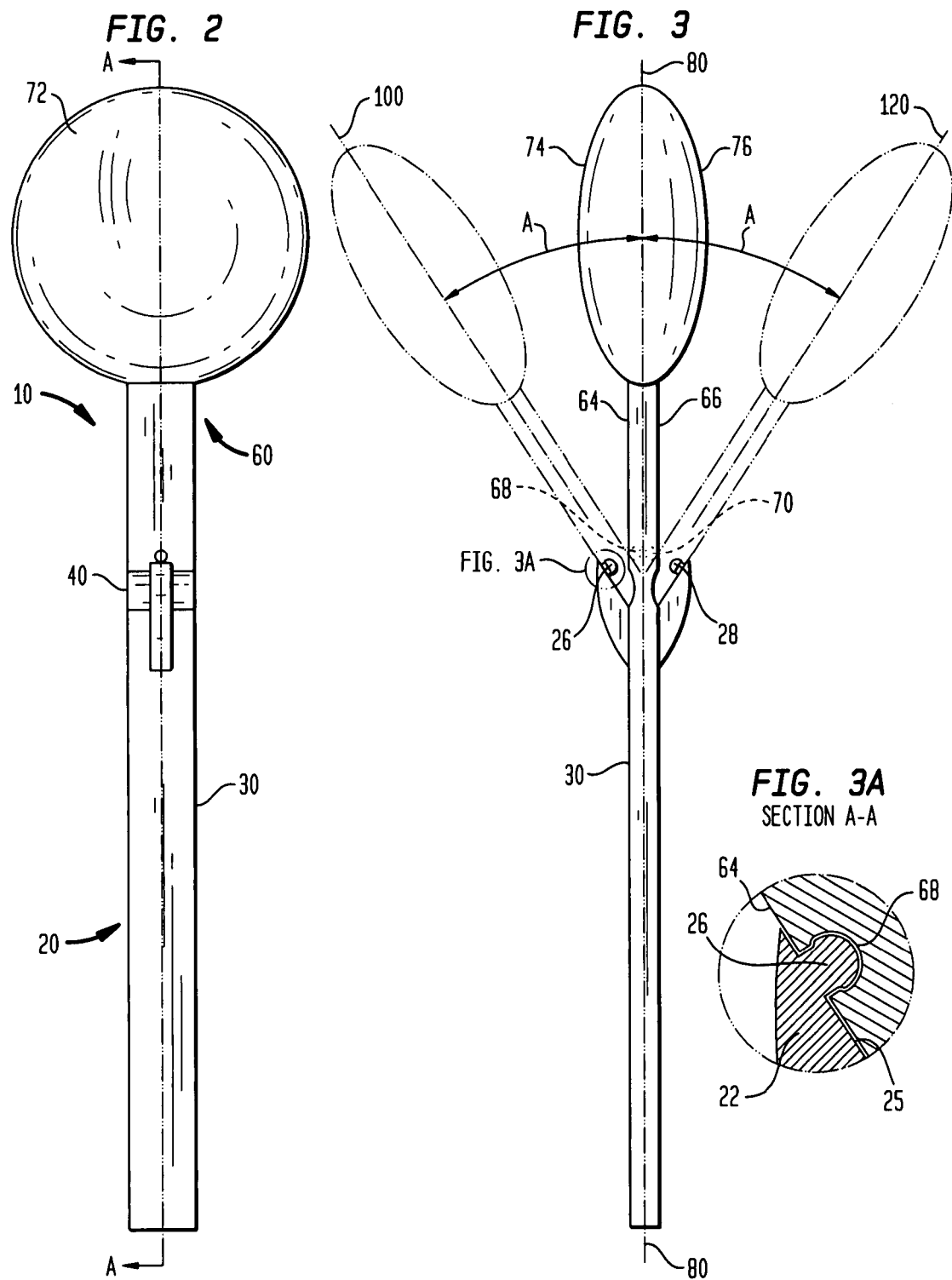

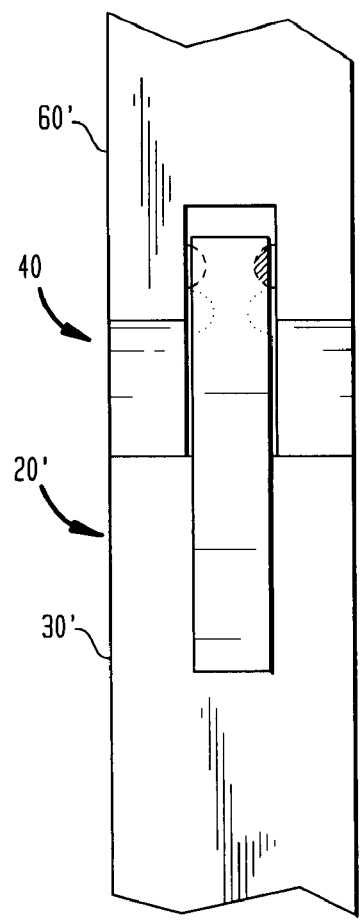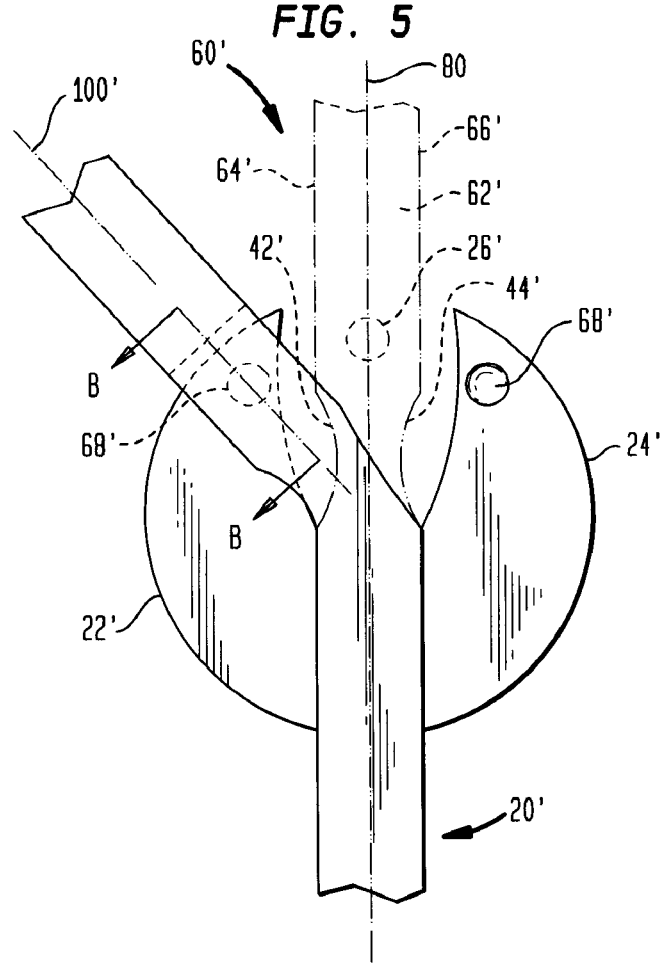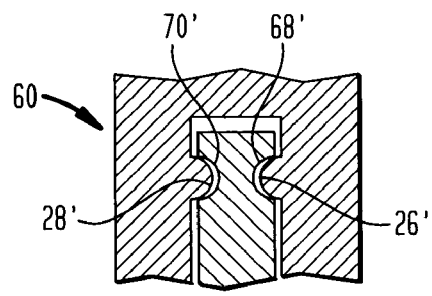

CONTROLLABLE SWAB DEVICE

BACKGROUND OF THE INVENTION

The present invention generally relates to swab devices. More specifically, the present invention relates to a swab device which may articulate into a first and/or second retained position.

Over the years, many types of applicator swabs have been made with the earliest of such swabs including a matted absorbent material such as cotton disposed on the end of a wooden stick. Cotton swabs are widely available in standard 3-inch (7.62 cm) rod lengths and ⅒-inch (2.54 mm) rod diameters, with the cotton applied at both ends of the rod. Coaxial alignment of the swab and the applicator stick is preferred in many uses.

In certain applications, a conventional coaxial swab and applicator handle is not convenient for use. For this reason, swabs may be set at an obtuse angle with respect to the applicator handle or stick. Such a use, for example, is application of medication accurately to portions of a person which would otherwise be difficult or impossible to reach. Swabs in this case generally have a handle member with a swab portion disposed at a predetermined angle thereof.

Another example where a conventional coaxial swab and applicator handle may not be convenient is for cleaning portions of the human ear. For instance, the funnel-shaped auricle of the ear may provide a surface for cleaning which lends itself to an applicator with a swab disposed at an obtuse angle thereto.

Swab devices may also have a structure which allows a swab portion to articulate in a plurality of directions. Such a structure may be beneficial for swabbing an area where the user does not want to apply a substantial amount of pressure. In this case, the swab may collapse or articulate in a direction opposed to that at which pressure is applied.

However, there are many applications in which it may be beneficial for a swab device to have a controllable portion that articulates in a first and second direction. Such a swab preferably comprises a controllable portion including a swab portion which may articulate in a first direction until it is retained in a first retained position, the controllable portion also having the ability to be released from the first retained position and articulate in a second direction until it is retained in a second retained position.

SUMMARY OF THE INVENTION

In accordance with one embodiment of the present invention, applicant has invented a swab device comprising a handle member having a swab portion and a hinge. The hinge is configured to allow the handle member to articulate in a first direction and a second direction. The handle member further includes a first stop member and a second stop member wherein the first stop member is configured to limit the articulation of the handle member in the first direction and the second stop member is configured to limit the articulation of the handle member in the second direction.

In accordance with this aspect of the swab device of the present invention, the handle member including the hinge is preferably configured as a unitary member. The hinge divides the handle member into a handle portion and a controllable portion. Preferably, the first stop member includes means for retaining the controllable portion in a first retained position and the second stop member includes means for retaining the controllable portion in a second retained position. The first and second stop portions may be removable from the swab device.

In accordance with another embodiment of the present invention, the handle portion and the controllable portion can each be a separate end member.

In accordance with another embodiment of the present invention, a swab device comprises a handle member having a hinge, a first stop member, and a second stop member. The swab device further includes a controllable portion having a swab portion, the controllable portion connected to the handle member by the hinge. Preferably, the hinge is configured to allow the controllable portion to articulate in first and second directions, wherein the first stop member is configured to limit the articulation of the controllable portion in the first direction and the second stop member is configured to limit the articulation of the controllable portion in the second direction.

In accordance with this aspect of the swab device of the present invention, the first stop member includes means for retaining the controllable portion in a first retained position and the second stop member includes means for retaining the controllable portion in a second retained position. In one embodiment of this aspect, the first stop member and the second stop member each include a protrusion and the controllable portion includes a first and second recess. The protrusion of the first stop member engages the first recess to retain the controllable portion in the first retained position. The protrusion of the second stop member engages the second recess to retain the controllable portion in the second retained position. The first and second stop portions may be removable from the swab device.

In accordance with yet another embodiment of the present invention, a swab device comprises a handle member including a first stop member having a first protrusion and a second stop member having a second protrusion. The swab device may further comprise a controllable portion including a swab portion, a first recess, and a second recess, the controllable portion connected to the handle member by a hinge. Preferably, the hinge is configured to allow the controllable portion to articulate into a first retained position and a second retained position, wherein the first protrusion and first recess are configured to retain the controllable portion in the first retained position and the second protrusion and second recess are configured to retain the controllable portion in the second retained position.

In yet another embodiment of the present invention, the swab device preferably has a rest position wherein the handle member and the controllable portion are coaxial, thereby aligned along the same vertical axis. In this embodiment, the hinge is preferably relaxed so that there is no potential energy stored in the swab device which would cause the controllable portion to articulate in a first or second direction.

In yet still another embodiment of the present invention, the controllable portion of the swab device may further include a first side surface and a second side surface. Preferably, the first stop member includes a first stop surface and the second stop member includes a second stop surface. The first side surface and the second side surface of the controllable portion are generally configured to contact respectively with the first stop surface and the second stop surface of the stop members.

In yet still another embodiment of the present invention, a method has been devised for using a swab device having a handle member including a swab portion and a hinge. The hinge is configured to allow the handle member to articulate into a first retained position and a second retained position.

The swab device further includes means for retaining the controllable portion in the first retained position and the second retained position. The method comprises the steps of articulating the controllable portion in a first direction and into the first retained position, and placing a first side of the swab portion in contact with an area to be swabbed. Preferably, the method further comprises articulating the controllable portion from the first retained position in a second direction and into the second retained position, and placing a second side of the swab portion in contact with an area to be swabbed.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 1 is front, isometric view of an example of a swab device of the present invention including a handle member having a swab portion and a hinge. The hinge divides the handle member into a handle portion and a controllable portion. The handle member includes means for retaining the controllable portion in a first and/or second retained position.

FIG. 1A is a front, enlarged, detailed view of the area surrounding the hinge of the swab device as shown in FIG. 1, including the means for retaining the controllable portion in a first and/or second retained position. In this exemplary embodiment, the means for retaining the controllable portion includes a first stop member having a first protrusion configured to mate with a first recess of the controllable portion and a second stop member having a second protrusion configured to mate with a second recess of the controllable portion.

FIG. 2 is a side, elevational view of a swab device of the present invention.

FIG. 3 is a front, elevational view of the swab device of the present invention wherein the swab device is shown articulating from a rest position into a first and/or second retained position.

FIG. 3A is a front, enlarged, detailed cross sectional view taken along line A-A of FIG. 2. of the swab device shown in FIG. 1, wherein the swab device is in the first retained position. Here, the mating of the first recess of the controllable portion and the first protrusion of the stop member are shown.

FIG. 4 is a partial, side, elevational, enlarged view of an alternative embodiment of a swab device including a handle member having a hinge and means for retaining the handle member in a first and/or second retained position.

FIG. 5 is a partial, front, elevational, enlarged view of the swab device of FIG. 4, wherein the swab device is shown articulating from a rest position into a first retained position.

FIG. 5A is a partial, side, elevational, enlarged cross sectional side view taken along line B-B of the swab device of FIG. 5.

DETAILED DESCRIPTION

Referring to the drawings, wherein like reference numerals refer to like elements, there is shown in FIGS. 1-3A, a swab device designated generally by reference numeral 10. However, it is to be understood that swab device 10 may vary in size and/or shape depending upon the particular function it is designed for. For instance, swab device 10 may be designed for medical applications. Here, swab device 10 may be designed to be received within an aperture in a body and/or designed for an area of the body that needs swabbing. Likewise, differently configured swab devices fall within the scope of the present invention. For example, certain of the below discussed elements of swab device 10 may vary according to the ultimate use of swab device 10.

As is best shown in the isometric view of FIG. 1, swab device 10 comprises a handle member 20 having a hinge 40 and a swab portion 72. Hinge 40 is configured to allow the handle member to articulate in a first direction and a second direction. Preferably, handle member 20 further includes a first stop member 22 and a second stop member 24 wherein first stop member 22 is configured to limit the articulation of handle member 20 in the first direction and second stop member 24 is configured to limit the articulation of handle member 20 in the second direction.

Handle member 20 including hinge 40 is preferably configured as a unitary member. Hinge 40 divides handle member 20 into a handle portion 30 and a controllable portion 60. Preferably, first stop member 22 includes means for retaining controllable portion 60 in a first retained position 100 and second stop member 24 includes means for retaining controllable portion 60 in a second retained position 120. In applications wherein articulation of controllable portion 60 does not need to be limited in a first and/or second direction, first and/or second stop portions 22, 24 may be removable from swab device 10.

Stop members 22, 24 for retaining controllable portion 60 in a first and/or second retained position 100, 120 are shown in FIGS. 1-5A. An exemplary embodiment of such means for retaining controllable portion 60 is shown in FIGS. 1-3A. In this embodiment of swab device 10, first stop member 22 includes a first stop surface 25 and a first protrusion 26 that preferably extends outwardly from first stop surface 25. Similarly, second stop member 24 includes a second stop surface 27 and a second protrusion 28 that preferably extends outwardly from second stop surface 27.

A more detailed example of the structure of first protrusion 26 and second protrusion 28 may be seen in FIG. 1A. In this example, first protrusion 26 has a neck or relief portion below a bulbous head. This exemplary relief portion is helpful for the bulbous head portion of first protrusion 26 to engage and preferably snap-fit into a first recess 68.

It should be understood that the subject matter of the invention encompasses any configuration of protrusions 26, 28 and recesses 68, 70 wherein protrusions 26, 28 may be pressure-fitted into recesses 68, 70. Further, the configuration of first protrusion 26 and second protrusion 28 should be such that a strong pressure-fit may be achieved between first protrusion 26 and first recess 68 and second protrusion 28 and second recess 70. Alternatively, the protrusions and recesses are preferably configured to later be disengaged by manual force if necessary.

Generally, the means for retaining the controllable portion in a first and/or second retained position includes a male end configured to be received within a female end. In FIGS. 1-3A of swab device 10, first protrusion 26 is a male end configured to be received and retained within a female end first recess 68. Other examples of configurations include, but are not limited to, first protrusion 26 having a male tapered end and first recess 68 having a female receiving end.

Further shown in FIGS. 1-3A, controllable portion 60 includes an elongated portion 62 preferably having a first side 64 and a second side 66. In this embodiment, controllable portion 60 has a first side surface 64 and a second side surface 66 because the elongated portion 62 of swab device 10 is rectangular. Preferably, first side surface 64 includes first recess 68 and second side surface 66 includes second recess 70. It is within the scope of the invention for the elongate portion to be other shapes, such as circular for example, wherein a first hemisphere of an elongated cylindrical shaft may have a first side surface 64 and a second hemisphere of the elongated cylindrical shaft may have a second side surface 66. Additionally, elongated shaft 62 may be configured as other geometric or non-geometric shapes having a first side surface 64 and a second side surface 66.

Swab portion 72 preferably has a first swab side 74 and a second swab side 76. It is within the scope of the invention for the swab device to be other shapes, such as spherical or ovular for example, that may not have easily defined first and second sides. Preferably, a first hemisphere of a spherical swab may have a first side surface 74 and a second hemisphere of the spherical swab may have a second side surface 76. Additionally, swab portion 62 may be configured as other geometric or non-geometric shapes having a first side surface 74 and a second side surface 76.

As shown best in FIG. 3, hinge 40 is configured to allow controllable portion 60 to articulate from a rest position 80 into a first retained position 100 and/or into a second retained position 120. An exemplary hinge 40 of the present invention, allows swab device 10 to articulate in a first and second direction substantially along a single plane.

As best seen in FIG. 1A, hinge 40 includes a first recess 42 and a second recess 44. It is within the scope of the present invention for hinge 40 to have other configurations. Preferably, hinge 40 is a living hinge as shown in FIGS. 1-3A, wherein swab device 10 is a unitary structure.

Alternatively, swab device 10 may comprise two or more separate pieces. Hinge 40 may therefore include some structure as part of handle portion 30 and some structure as part of controllable portion 60.

In such embodiments, hinge 40 may have a male protrusion extending outwardly from a bottom surface of controllable portion 60 which may be configured to mate with a female receiving portion located on a top surface of handle portion 30. Alternatively, in yet another embodiment, hinge 40 may have a male protrusion extending outwardly from a top surface of handle portion 30 which may be configured to mate with a female receiving portion located on a bottom surface of controllable portion 60.

When handle portion 30, hinge 40, and controllable portion 60 are coaxial, swab device 10 is in rest position 80. Rest position 80 may also be defined as the central axis of swab device 10 in the rest position. In an exemplary embodiment, as shown in FIGS. 1-3A, swab device 10 is a rectangular solid with a central axis.

It should be understood that the features of swab device 10 are preferably symmetric about a central axis. In a preferred embodiment, handle member 20 is generally a rectangular solid having a left and right side symmetric about central axis 80, as best seen in FIG. 3. Preferably, similar features on the left and right sides of swab device 10 have symmetrical configurations. For instance, first stop member 22 and second stop member 24 are preferably symmetrical about center axis 80 and have symmetric configurations.

In one embodiment, controllable portion 60 may articulate in a first direction from rest position 80 and into a first retained position 100. Preferably, first protrusion 26 and first recess 68 are configured to retain controllable portion 60 in first retained position 100. After controllable portion 60 is retained in first retained position 100, first surface 64 of controllable portion 60 may contact first stop surface 25 of first stop member 22. First stop member 22 is configured to prohibit controllable portion 60 from articulating any further in the first direction.

While swab device 10 is in first retained position 100, stop member 22 prohibits controllable portion 60 from articulating any further in the first direction. When pressure is applied to a surface being swabbed with swab portion 72, stop member 22 prohibits controllable portion 60 from articulating out of first retained position 100. Stop member 22 is configured to keep controllable portion 60 in first retained position 100 whether swab surface 74 or 76 is in contact with a surface being swabbed.

Preferably, stop member 22 is configured to ensure controllable portion 60 does not move out of first retained position 100 when swab surface 76 is being used for swabbing. A user may apply pressure to a surface with swab surface 76 without having controllable portion 60 articulate further in the first direction.

In first retained position 100, side surface 64 of elongate portion 62 is preferably pressed against side surface 25 of stop member 22 when swab surface 76 is being used for swabbing. Further, protrusion 26 and recess 68 are mated when controllable portion 60 is in first retained position 100.

Controllable portion 60 may be released from first retained position 100 and articulated into second retained position 120 without having to touch swab portion 72. This is an important aspect of swab device 10 for use in the non-limiting example of medical applications. Medical instruments must always remain sterile when used on patients. The less a user touches with his or her hands a portion of a medical device which comes in contact with a patient's body, the less chance of contaminating that portion of the device and subsequently the less chance of contaminating the patient.

Sufficient pressure to disengage recess 68 from protrusion 26 must be applied to controllable portion 60 to release controllable portion 60 from first retained position 100. A user of swab device 10 may press side surface 64 of elongate portion 62 against a preferably sterile surface to disengage recess 68 and protrusion 26. Alternatively, a user of swab device 10 may disengage controllable portion 60 from first retained position 100 by pressing side surface 74 or side surface 76 of swab portion 72 against an area being swabbed or an area yet to be swabbed. In disengaging controllable portion 60 from first retained position 100 in any of the non-limiting described manners, a user does not have to touch swab portion 72 with his or her hands. Once controllable portion 60 is released from first retained position 100, controllable portion 60 may then articulate into second retained position 120.

While controllable portion 60 is in second retained position 100, stop member 24 prohibits controllable portion 60 from articulating any further in the second direction. When pressure is applied to a surface being swabbed with swab portion 72, stop member 24 prohibits controllable portion 60 from articulating out of second retained position 120. Stop member 24 is configured to keep controllable portion 60 in second retained position 100 whether swab surface 74 or 76 is in contact with a surface being swabbed.

Preferably, stop member 24 is configured to ensure controllable portion 60 does not move out of second retained position 100 when swab surface 74 is being used for swabbing. In this case, a user may apply pressure to a surface with swab surface 74 without having controllable portion 60 articulate further in the second direction.

In second retained position 120, side surface 66 of elongate portion 62 is preferably pressed against side surface 27 of stop member 24 when swab surface 74 is being used for swabbing. Further, protrusion 28 and recess 70 are mated when controllable portion 60 is in second retained position 120.

Controllable portion 60 may further be released from second retained position 120 and articulated back into first retained position 100 without a user having to touch swab portion 72. Sufficient pressure to disengage recess 70 from protrusion 28 must be applied to controllable portion 60 to release controllable portion 60 from second retained position 120. A user of swab device 10 may press side surface 66 of elongate portion 62 against a preferably sterile surface to disengage recess 70 and protrusion 28. Alternatively, a user of swab device 10 may disengage controllable portion 60 from second retained position 120 by pressing side surface 74 or side surface 76 of swab portion 72 against an area being swabbed or an area yet to be swabbed. In disengaging controllable portion 60 from second retained position 120 in any of the non-limiting described manners, a user does not have to touch swab portion 72 with his or her hands. Once controllable portion 60 is released from second retained position 120, controllable portion 60 may articulate back into first retained position 100 if necessary for a particular application of swab device 10.

First retained position 100 defines the position of the central axis of controllable portion 60 in first retained position 100. Preferably, controllable portion 60 may articulate 15 to 75 degrees from rest position 80 to first retained position 100. More preferably, controllable portion articulates 30 to 60 degrees between rest position 80 and first retained position 100. In other embodiments, first stop member 22 may be configured to allow controllable portion 60 to articulate between rest position 80 and first retained position 100 from 0 to 90 degrees.

In another embodiment, controllable portion 60 may articulate in a second direction opposite the first direction from first retained position 100 into second retained position 120. Preferably, second protrusion 28 and second recess 70 are configured to retain controllable portion 60 in second retained position 120. After controllable portion 60 is retained in second retained position 120, second surface 66 of controllable portion 60 may contact second top surface 27 of second stop member 24. Second stop member 24 is configured to prohibit controllable portion 60 from articulating any further in the second direction.

Second retained position 120 defines the position of the central axis of the controllable portion 60 in second retained position 120. Preferably, controllable portion 60 may articulate 45 to 135 degrees from first retained position 100 to second retained position 120. More preferably, controllable portion articulates 65 to 115 degrees between first retained position 100 and second retained position 120. In other embodiments, first stop member 22 may be configured to allow controllable portion 60 to articulate between first retained position 100 and second retained position 120 from 0 to 180 degrees.

An alternative embodiment of swab device 10 is shown in FIGS. 4-5A denoted by swab device 10'. The structure of swab device 10' is much like that of swab device 10. Swab device 10' includes a handle member 20' having a hinge 40' and means for retaining handle member 20' in a first retained position 100' and a second retained position 120'.

Hinge 40' divides handle member 20' into a handle portion 30' and a controllable portion 60'. Preferably, first stop member 22' and controllable portion 60' includes means for retaining controllable portion 60' in a first retained position 100' and second stop member 24' and controllable portion 60' includes means for retaining controllable portion 60' in a second retained position 120'.

In applications wherein articulation of controllable portion 60' does not need to be limited in a first and/or second direction, first and/or second stop portions 22', 24' may be removable from swab device 10'.

An example of means for retaining controllable portion 60' is shown in FIGS. 4-5A. In this embodiment of swab device 10', stop members 22', 24' include a first recess 68' and a second recess 70'. Controllable portion 60' includes protrusions 26', 28'. First recesses 68' of stop members 22', 24' are configured to mate with protrusion 26' of controllable portion 60'. Second recesses 70' of stop members 22', 24' are configured to mate with protrusion 28' of controllable portion 60'.

A more detailed example of the structure of the means for retaining the controllable portion 60' in a first and/or second retained position may be seen in FIG. 5A. In this example, a cross-sectional view of first stop member 22' is shown. In this view, controllable portion 60' is in the first retained position. Here, protrusion 26' of controllable portion 60' is mated with recess 68' of first stop member 22' and protrusion 28' of controllable portion 60' is mated with recess 70' of first stop member 22'.

It should be understood that the subject matter of the invention encompasses any configuration of protrusions 26', 28' and recesses 68', 70' wherein protrusion 26', 28' may be pressure-fitted into recesses 68', 70'. Further, the configuration of protrusions 26', 28' should be such that a strong pressure-fit may be achieved between protrusions 26', 281 and recesses 68', 70'. Alternatively, the protrusions and recesses are preferably configured to later be disengaged by manual force if necessary.

Generally, the means for retaining the controllable portion in a first and/or second retained position includes a male end configured to be received within a female end. In FIGS. 4-5A of swab device 10', protrusion 26' is a male end configured to be received and retained within a female end recess 68'. Other examples of configurations include, but are not limited to, protrusion 26' having a male tapered end and recess 68' having a female receiving end.

In this embodiment, while controllable portion 60' is in first retained position 100', stop member 22' prohibits controllable portion 60' from articulating any further in the first direction. When pressure is applied to a surface being swabbed with swab portion 72', stop member 22' prohibits controllable portion 60' from articulating out of first retained position 100'. Stop member 22' is configured to keep controllable portion 60' in first retained position 100' whether swab surface 74' or 76' is in contact with a surface being swabbed.

When controllable portion 60' is in first retained position 100', protrusion 26' of controllable portion 60' is mated with recess 68' of first stop member 22' and protrusion 28' of controllable portion 60' is mated with recess 70' of first stop member 22'.

Controllable portion 60' may be released from first retained position 100' and articulated into second retained position 120' without having to touch swab portion 72'. This is an important aspect of swab device 10' for use in the non-limiting example of medical applications. Medical instruments must always remain sterile when used on patients. The less a user touches with his or her hands a portion of a medical device which comes in contact with a patient's body, the less chance of contaminating that portion of the device and subsequently the less chance of contaminating the patient.

Sufficient pressure to disengage protrusions 26', 28' of controllable portion 60' from recesses 68', 70' of stop member 22' must be applied to controllable portion 60' to release controllable portion 60' from first retained position 100'. A user of swab device 10' may press side surface 64' of elongate portion 62' against a preferably sterile surface to disengage protrusions 26', 28' and recesses 68', 70' of stop member 22'. Alternatively, a user of swab device 10' may disengage controllable portion 60' from first retained position 100' by pressing side surface 74' or side surface 76' of swab portion 72' against an area being swabbed or an area yet to be swabbed. In disengaging controllable portion 60' from first retained position 100' in any of the non-limiting described manners, a user does not have to touch swab portion 72' with his or her hands. Once controllable portion 60' is released from first retained position 100', controllable portion 60' may then articulate into second retained position 120'.

While controllable portion 60' is in second retained position 100', stop member 24' prohibits controllable portion 60' from articulating any further in the second direction. When pressure is applied to a surface being swabbed with swab portion 72', stop member 24' prohibits controllable portion 60' from articulating out of second retained position 120'. Stop member 24' is configured to keep controllable portion 60' in second retained position 100' whether swab surface 74' or 76' is in contact with a surface being swabbed.

When controllable portion 60' is in second retained position 120', protrusion 26' of controllable portion 60' is mated with recess 68' of second stop member 24' and protrusion 28' of controllable portion 60' is mated with recess 70' of second stop member 24'.

Controllable portion 60' may further be released from second retained position 120' and articulated back into first retained position 100' without a user having to touch swab portion 72'. Sufficient pressure to disengage protrusions 26', 28' of controllable portion 60' from recesses 68', 70' of stop member 24' must be applied to controllable portion 60' to release controllable portion 60' from second retained position 120'. A user of swab device 10 may press side surface 66' of elongate portion 62' against a preferably sterile surface to disengage protrusions 26', 28' from recesses 68', 70' of stop member 24'. Alternatively, a user of swab device 10' may disengage controllable portion 60' from second retained position 120' by pressing side surface 74' or side surface 76' of swab portion 72' against an area being swabbed or an area yet to be swabbed. In disengaging controllable portion 60' from second retained position 120' in any of the non-limiting described manners, a user does not have to touch swab portion 72' with his or her hands. Once controllable portion 60' is released from second retained position 120', controllable portion 60' may articulate back into first retained position 100' if necessary for a particular application of swab device 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A swab device comprising:
a handle member having a longitudinal axis along which a swab portion and a hinge are located, said swab portion having a first swab side anterior to the longitudinal axis and a second swab side posterior the longitudinal axis, said hinge configured to allow said swab portion to articulate in both a first direction and a second direction, said first direction and said second direction being at an angle intersected by said longitudinal axis;
a first stop member and a second stop member wherein said first stop member is configured to limit the articulation of said swab portion in said first direction and said second stop member is configured to limit the articulation of said swab portion in said second direction;
a protrusion on each of said first and second stop members; and a first and second recess on said controllable portion, wherein said protrusion of said first stop member engages said first recess to retain said controllable portion in a first retained position and said protrusion of said second stop member engages the second recess to retain said controllable portion in a second retained position.

2. The swab device of claim 1, wherein said handle member including said hinge is configured as a unitary member.

3. The swab device of claim 1, where said hinge divides said handle member into a handle portion and a controllable portion.

4. The swab device of claim 3, wherein said first stop member includes means for retaining said controllable portion in a first retained position and said second stop member includes means for retaining said controllable portion in a second retained position.

5. The swab device of claim 1, wherein said first and second stop members are removable.

6. A swab device comprising:
a handle member having a hinge, a longitudinal axis, a first stop member, and a second stop member;
a controllable portion having a longitudinal axis and a swab portion located along the longitudinal axis, said swab portion having a first swab side anterior to the longitudinal axis and a second swab side posterior the longitudinal axis, said controllable portion connected to said handle member by said hinge, said hinge configured to allow said controllable portion to articulate in both first and second directions, said first direction and said second direction being at an angle intersected by the longitudinal axis of said handle member, wherein said first stop member is configured to limit the articulation of the controllable portion in said second direction;
a protrusion on each of said first and second stop members; and a first and second recess on said controllable portion, wherein said protrusion of said first stop member engages said first recess to retain said controllable portion in a first retained position and said protrusion of said second stop member engages the second recess to retain said controllable portion in a second retained position and said second stop member is configured to limit the articulation of said controllable portion in said second direction.

7. The swab device of claim 6, wherein said first stop member includes means for retaining said controllable portion in a first retained position and said second stop member includes means for retaining said controllable portion in a second retained position.

8. The swab device of claim 7, wherein said first and second stop portions are removable.

9. The swab device of claim 6, wherein said handle member including said hinge and the controllable portion is configured as a unitary member.

10. A method of using a swab device having a handle member including a longitudinal axis along which a swab portion and a hinge are located, said swab portion having a first swab side anterior to the longitudinal axis and a second swab side posterior the longitudinal axis, said hinge configured to allow said swab portion to articulate into both a first retained position and a second retained position, said first and second retained positions being at an angle intersected by said longitudinal axis, and a protrusion on each of said first and second stop members, and a first and second recess on said controllable portion, wherein said protrusion of said first stop member engages said first recess to retain said controllable portion in the first retained position and said protrusion of said second stop member engages the second recess to retain said controllable portion in the second retained position, the method comprising the steps of:
- articulating said controllable portion in a first direction and into said first retained position;
- placing a first side of said swab portion in contact with an area to be swabbed;
- articulating said controllable portion from said first retained position in a second direction and into said second retained position; and
- placing a second side of the swab portion in contact with an area to be swabbed.

11. A swab device comprising:
a handle portion having a longitudinal axis;
a hinge portion; and
a controllable portion having a swab portion at a distal end thereof, said swab portion having a first swab side and a second swab side;
said hinge portion connecting said handle portion and said controllable portion;
said controllable portion being movable between a first position with the controllable portion and first swab side extending angularly from said longitudinal axis in a first direction to a second position with the controllable portion and second swab side extending angularly from said longitudinal axis in a second opposite direction;
said controllable portion being prevented from movement beyond the first position by a first stop member and from movement beyond said second position by a second stop member;
a protrusion on each of said first and second stop members;
and a first and second recess on said controllable portion, wherein said protrusion of said first stop member engages said first recess to retain said controllable portion in a first retained position and said protrusion of said second stop member engages the second recess to retain said controllable portion in a second retained position.

* * * * *